United States Patent [19]

van der Wal

[11] Patent Number: 4,820,286
[45] Date of Patent: Apr. 11, 1989

[54] AUTOMATIC INJECTOR

[75] Inventor: Gillis P. van der Wal, Olst, Netherlands

[73] Assignee: Duphar International Research B.V., Weesp, Netherlands

[21] Appl. No.: 48,884

[22] Filed: May 12, 1987

[30] Foreign Application Priority Data

May 15, 1986 [NL] Netherlands .......................... 8601228

[51] Int. Cl.⁴ ............................................ A61M 37/00
[52] U.S. Cl. ....................................... 604/89; 604/90; 604/191; 604/134
[58] Field of Search ................... 604/89, 90, 191, 134, 604/135, 136, 143, 144

[56] References Cited

U.S. PATENT DOCUMENTS

| | | | |
|---|---|---|---|
| 4,226,236 | 10/1980 | Genese | 604/89 |
| 4,394,863 | 7/1983 | Bartner | 604/90 |
| 4,496,344 | 1/1985 | Kamstra | 604/90 |
| 4,573,971 | 3/1986 | Kamstra | 604/191 |
| 4,613,326 | 9/1986 | Szwarc | 604/89 |

Primary Examiner—Allen M. Ostrager
Attorney, Agent, or Firm—Stevens, Davis, Miller & Mosher

[57] ABSTRACT

The invention relates to an automatic injector for injecting one or more injection liquids, comprising an assembly of a discharge mechanism, a cartridge in a cartridge holder, and an outer sleeve which is telescopically slidable around the cartridge holder, which cartridge comprises a barrel, in the barrel a piston and a number of separating stoppers equal to one less than the number of injection liquids, a needle holder with injection needle and optionally a by-pass for injection liquid. The injector is suitable for accommodating a solid and a solvent therefor, and for that purpose comprises a passable stopper between solid and solvent and a solvent by-pass in the barrel wall or in the passable stopper, in which, by a single or repeated operation of telescoping external parts of the injector solvent can pass the passable stopper and can reach the solid, as a result of which the injector can be made ready for use.

17 Claims, 3 Drawing Sheets

AUTOMATIC INJECTOR

The invention relates to an automatic injector for injecting one or more injection liquids, in which, prior to use, different substances which are not allowed to be in contact with each other for a long period of time can be stored separately, comprising an assembly of a discharge mechanism, a cartridge in a cartidge holder, and an outer sleeve which is telescopically slidable around the cartridge holder, the cartridge comprising:

a hollow, substantially cylindrical barrel which is open at its rear end;

a piston which is movable in the barrel and seals same, a number of separating stoppers equal to one less than the number of injection liquids, said separating stoppers being movable in the barrel and having circumferences that adjoin the inner wall of the barrel in a sealing manner, thereby keeping the injection liquids in the barrel separated from each other prior to use of the injector, a needle holder connected to the front end of the barrel in a sealing manner and comprising a neck for sealingly gripping a needle, which needle, if desired, is covered by a sheath to maintain said needle in a sterile condition, and in case the injector is destined for at least two injection liquids, a by-pass for injection liquid in front of said separating stopper or front separating stopper, for permitting said injection liquid or liquids behind the stopper or stoppers to reach the injection needle, when during use of this injector the stopper or stoppers is or are moved forward, said by-pass extending in the longitudinal direction over a distance slightly larger than that of the separating stopper or collection of separating stoppers, so that said stopper or collection of stoppers in their ultimate forward position does or do not cover the rear end of said by-pass.

Such a injector in known from the U.S. Pat. Nos. 4,529,403 and 4,394,863. The injection needle of the injectors disclosed in said patent specifications comprises a needle guard of a resilient material which keeps the needle in a sterile condition during storage of the injectors and, when the injectors are used, serves as a shock absorber for the cartridge. Such a needle-guard is an excellent provision and is preferably also used in the injector according to the present invention.

Automatic injectors have been designed in particular for use by human beings who at a given instant, which is not known beforehand, have to administer an injection into their own body. These beings include, for example, soldiers after having been exposed to an enemy's battle gas, for example, a nerve gas. It therefore will be obvious that automatic injectors must satisfy stringent requirements regarding their reliability in use. Such injectors are usually stored for many years at a time and in addition, after having been handed over to the potential users, will be kept by said users for long periods of time under varying conditions; the proper operation of the injectors must be sufficiently ensured. In fact, at the critical instant the user's life may depend on the operation of the injector. Therefore, automatic injectors must satisfy stringent requirements as for their storage stability.

The administration of several medicaments or antidotes is often necessary in particular for military use, inter alia, because, of course, nature and composition of the battle gas used by the enemy are not known beforehand and/or to achieve an effective therapy. Some medicaments, which are sufficient storage-stable as solids, are not stable for the required long storage period after having been dissolved in a solvent to form a solution suitable for injection. An injector in which a solid as such can be accommodated might provide a solution to the problem of storing these medicaments. It is remarkable that such an automatic injector has, so far as known, not yet been realised. Obviously, the technical problems occuring in developing such an injector have so far been prohibitive.

The present invention provides a solution to the above problem, starting from the recognition that the instability of such medicament solutions is always relative, i.e. that such substances always have a certain, albeit restricted, stability in solution. It has now been found that an injector can be used for the separate storage of at least two different substances which may not be in contact with each other for a long period of time, in which one of the substances in the injector is solid and can be injected as an injection liquid only after dissolving in a solvent, if by a simple operation prior to the actual use the injector is made ready for use. This operation of making the injector ready for use may take place a shorter or longer time before the use of the injector, depending on the stability of the medicament solution, either by the potential user himself, or by the person who hands over the injector to the user. In order to minimise the possibility of mistakes, it is recommendable to make the injectors ready for use immediately before or upon providing the injectors to the potential users, for example, soldiers in the field. This is advisable in all those cases in which the medicaments or antidotes in solution are sufficiently stable for a period of at least a few hours a day. Making the injector ready for use is a simple operation, namely performing once or repeatedly a simple telescoping movement of external parts of the injector with respect to each other, which operation can easily be carried out.

In order to be able to use an injector of the type mentioned in the opening paragraph for the separate storage of at least two different substances one of which is solid and can be injected as an injection liquid only after dissolving in a solvent, in which at the same time the advantages known from the U.S. Pat. No. 4,529,403 mentioned hereinbefore, e.g. easy handlability, rapidly ready for use, and relatively uncomplicated which is in favour of the reliability, have been maintained, the injector according to the invention is designed in such a way, that the discharge mechanism is in operative relationship with the piston via a plunger and is capable of telescoping movement relative to the cartridge holder, permitting the injector to be made ready for use by a single or repeated forward movement of the piston in the barrel, that prior to using the injector, the cartridge at its front end is provided with a sealing means to prevent injection liquid from leaving the injector via the needle during making the injector ready for use, that a passable stopper, movably provided in the barrel in front of the piston and which, prior to making the injector ready for use, adjoins the inner wall of the barrel in a circumferentially sealing manner and keeps the solid separated from the solvent, and that a solvent by-pass for liquid is situated in the barrel wall over a length slightly exceeding the length of the passable stopper, or in the passable stopper, said solvent by-pass permitting the solvent to pass the passable stopper and reach the solid in front of said stopper and dissolve same upon making the injector ready for use.

The injector according to invention is particularly flexible, because any desired number of injection liquids can be injected therewith dependent on the chosen number of separating stoppers and on the length of the by-pass for injection liquid. For practical considerations it is desirable to restrict the number of injection liquids to at most four.

The solid may be present in the form of an, optionally lyophilized, powder, a tablet, granules, crystals, pills, and the like. The term "solid" should be interpreted widely and also includes a medicament which can be injected only afters dilution with a diluent. Such medicaments may be accommodated in the injector in the form of pastes or concentrated solutions which cannot be injected as such. The solvent by-pass then serves as a by-pass for the diluent. The terms "solid" and "solvent" for the said solid, as used in the specification and claims, should therefore be understood to include "medicament to be diluted before injection" and "diluent" for such a medicament.

If, in addition to a solid and a solvent therefor, the injector comprises one or more injection liquids, these may be situated in front of a or behind the compartments comprising solid and solvent. In the former case, which is to be preferred for practical reasons, the solid is enclosed between the passable stopper and the separating stopper or the rear separating stopper, and the solvent for the solid between the piston and the passable stopper. In the latter case the solvent for the solid is enclosed between a separating stopper and the passable stopper, injection liquid being accommodated in the injector behind said separating stopper.

Due to the simplicity of the operation for making ready for use, the injector according to the invention is also particularly suitable for packaging in a multi-unit pack, for example, a multi-unit box, in which, when the injectors are handed over to the potential users, the injectors can be made ready for use collectively, for example, by performing a single or repeated telescoping movement of a wall of the box.

The following explanation serves to elucidate the operation of making the injector according to the invention ready for use. As a result of the inward telescoping movement of the discharge mechanism relative to the cartridge holder the piston in the barrel is moved forward. The pressure exerted on the piston propagates to the passable stopper via the liquid or liquids between piston and passable stopper. Therefore, said passable stopper is moved forward over the same distance as the piston until its rear face is present beyond the rear end of the solvent by-pass. Because the cartridge is sealed at its front end, pressure is built up in the barrel under the influence of which the solvent behind the passable stopper passes said stopper via the by-pass. When the force exerted to move the discharge mechanism relative to the cartridge holder is removed, the pressure built up in the barrel provides the piston resuming its initial position, the passable stopper remaining in its place so that, under the influence of the same pressure, air from the space in front of the solvent by-pass (the compartment for solid) flows backwards through the by-pass. Dependent on the relative dimensions of the compartment for solid and the room destined for the solvent respectively, a smaller or larger portion of the solvent has reached the solid in the compartment for solid. This operation may be repeated ("pumping") until sufficient solvent has been added to enable the solid to dissolve to an injection liquid. During this pumping operation, the injector should be kept with its front or its nose downward so as to ensure the transfer of the solvent via the by-pass to the compartment for solid. With the usual relative dimensions of the rooms necessary to accommodate solid and solvent, approximately five times "pumping" is usually sufficient to transfer so much solvent to the compartment for solid that a solution is obtained which is suitable for injection. The injector is now ready for use and can be applied by the user at any desired moment to administer an injection.

In order to be able to perform the above operation of making the injector ready for use it is essential for the cartridge to be sealed at its front end. Otherwise, injection liquid would leak away and leave the injector via the needle as a result of the pressure build-up in the barrel during making the injector ready for use. The barrel may comprise at its front end a sealing stopper or membrane which keeps the barrel closed during making the injector ready for use, but which bursts open or is pierced upon using the injector, thus uncovering the passage for the injection liquid or liquids so that it/they can leave the injector and be injected. However, the injector according to the invention is preferably constructed in such a way that the injection needle prior to use of the injector is covered by a sleeve-like needle guard of a resilient material which is connected with its open end around the neck of the needle holder and which in the proximity of its closed end keeps the front end portion of the needle tightly enclosed. This is to be understood to also include that situation in which the tip of the needle has been inserted into the rubber of the closed end of the needle guard to such an extent that the needle opening is sealed completely by the rubber. The object of such a needle guard hence is twofold, namely keeping the injection needle in a sterile condition before use of the injector and sealing the cartridge at its front end. When using the injector, the closed end of the needle guard is pierced by the tip of the needle, after which the injection liquid or liquids can leave the injector via the injection needle as described in U.S. Pat. No. 4,529,403 mentioned hereinbefore.

The by-pass for injection liquid in front of the separating stopper or front separating stopper may be provided in the barrel and, dependent on the material from which the barrel is manufactured, may be constructed in various manners as will be described hereinafter for the solvent by-pass. A glass barrel is usually preferred in which in a favourable embodiment the by-pass comprises at least one outwardly projecting bulge of the barrel wall extending in the logitudinal direction of the barrel. In an equally favourable embodiment the by-pass for injection liquid comprises at least one radially inwardly directed ridge on the inner wall of the barrel or a separate plastics fitting mounted within the wall of the barrel, said ridge or fitting extending in the longitudinal direction of the barrel and having a length slightly exceeding the length of the separating stopper or collection of separating stoppers, so that upon use of the injector said stopper or stoppers is or are deformed by contact with said ridge or fitting, a passage for the injection liquid or liquids behind said stopper or stoppers being formed allowing said liquid or liquids to pass said stopper or stoppers. Of course, various other embodiments of the by-pass are possible without departing from the scope of the present invention.

In a preferred embodiment the injector according to the invention is constructed in such a way that the injection needle is connected to the barrel by means of a needle holder which comprises a collar sealingly connecting the needle holder to the front end of the barrel and keeping the barrel in radially spaced relationship from the cartridge holder. As a result of this, also when using one or more outwardly projecting bulges of the barrel wall as a by-pass for injection liquid and/or solvent, the inner surface of the cartridge holder can remain rotationally symmetric. The cartridge holder thus need not comprise a recess or recesses to be able to accommodate therein such a bulge or such bulges of the barrel wall. As a result of this the assembly is facilitated considerably while, when using the injector as described in U.S. Pat. No. 4,529,403 mentioned hereinbefore, the cartridge can more easily move forward in the holder.

The injector in this latter embodiment is preferably constructed in such a way that the injection needle is connected to the barrel by means of a needle holder, comprising a collar with which the needle holder is sealingly connected to the front end of the barrel, a neck in which the injection needle is connected, a hollow, substantially cylindrical shaft between collar and neck, and a by-pass for injection liquid in the wall of the shaft allowing the injection liquid or liquids behind the separating stopper or stoppers to reach the injection needle when during use of the injector the stopper or stoppers is or are moved forward into the shaft of the needle holder. For technical reasons of production a by-pass for injection liquid provided in the wall of the needle holder is to be preferred to a by-pass in the barrel wall because such a needle holder having a by-pass can be manufactured simply, preferably by injection moulding, from a suitable synthetic material. For example, the by-pass for injection liquid in the wall of the shaft of the needle holder may be formed in a suitable manner as shown and described in U.S. Pat. No. 4,529,403 mentioned hereinbefore. In such a construction, said by-pass comprises at least one slot recessed in the inner wall of the shaft and extending in the longitudinal direction of the shaft from the rear end of the shaft and communicating with the open rear end of the injection needle via at least one slot radially recessed in the rear face of the neck of the needle holder. In another likewise suitable embodiment the inner wall of the shaft of the needle holder comprises at least one ridge which extends from the rear end of the shaft in the longitudinal direction of the shaft so that when using the injector the separating stopper or stoppers is or are deformed by contact with the said ridge, a passage for injection liquid behind the said stopper or stoppers being formed permitting said liquid to pass the stopper or stoppers, the rear face of the neck of the needle holder or the front face of the separating stopper or front separating stopper comprising a plurality of spacing supports allowing said liquid, after passing the stopper or stoppers, to reach the open rear end of the injection needle. When the rear face of the neck of the needle holder comprises spacing supports for passing the injection liquid, said spacing supports may be constructed as ridges provided radially on said rear face as an extension of the ridges on the inner wall of the shaft.

It is advantageous for the injector to comprise means to prevent a forward movement of the cartridge in the cartridge holder during making the injector ready for use. Otherwise the possibility might exist that during making the injector ready for use the barrel with the needle connected thereto might move forward into the cartridge holder, as a result of which the needle tip might emanate forward from the injector. Suitable means to prevent this are, for example, a plurality of radially provided cams or a circumferential edge on the inner wall of the cartridge holder which keeps the cartridge locked against a forward movement in the cartridge holder during making the injector ready for use, but which easily allows passage of the cartridge upon the actual use of the injector.

It is of essential importance that the injector can easily be made ready for use by a suitable choice of the mutually telescopically slidable external parts of the injector. In a preferred embodiment the injector according to the invention is constructed in such a way that the discharge mechanism can be moved telescopically relative to the outer sleeve comprising the cartridge holder locked therein against forward movement, so that by a single or repeated operation of inwardly telescoping the discharge mechanism relative to the outer sleeve, as a result of which the piston is moved forward in the barrel, the injector is made ready for use. In another, likewise suitable, embodiment the injector is constructed in such a way that the cartridge holder is telescopically movable relative to the outer sleeve comprising the discharge mechanism locked therein against rearward movement, so that by a single or repeated operation of inwardly telescoping the cartridge holder relative to the outer sleeve, as a result of which the piston is moved forward in the barrel, the injector is made ready for use. The discharge mechanism usually comprises a power source, for example a coil spring, which upon use of the injector can move the cartridge from a inoperative to an operative condition, locking means to control the actuation of the power source, and safety device to block said locking means. The telescopic movement mentioned hereinbefore of or relative to the discharge mechanism is to be understood to means also a movement of a relative to a component of the discharge mechanism, for example, the safety device.

It is advantageous, prior to making the injector ready for use, to fix the mutually telescopically slidable external parts of the injector, i.e. the discharge mechanism or the cartridge holder relative to the outer sleeve, by means of a detachable locking member for prevenging unintentional movement of said parts relative to each other. In the first-mentioned preferred embodiment a locking ring or locking clip may be used for this purpose which serves to fix the distance between the discharge mechanism and the outer sleeve and which can easily be detached to allow making the injector ready for use.

If desired, the injector may comprise an indication that the injector is ready for use, so that the user can easily ascertain that the operation of making the injector ready for use has been carried out. In case a detachable locking member is used, a good indication is, for example, the provision of conspicuous colour (signal colour) on the locking member or on that portion of the injector which prior to making the injector ready for use is covered by the locking member.

Moreover it is favourable to fix the distance over which the external parts of the injector have to be telescoped relative to each other upon making the injector ready for use, the so-called "pumping stroke". In the embodiment in which a detachable locking member is used to fix the distance between the mutually telescopic parts relative to each other before the injector is made ready for use, said "pumping stroke" may be provided to correspond to the distance fixed by the locking member. Of course there are various other possibilities to fix the "pumping stroke". It will be obvious that various components of the injector according to the invention, for example, the outer sleeve, the cartridge holder and parts of the discharge mechanism, are preferably manufacatured from a form-retaining, slightly resilient synthetic material, for example, by injection moulding. It is advantageous to construct the cartridge holder in such a manner that the portion covering the barrel has a five-sided to fourteen-sided cross-section as described in Netherlands Patent Application No. 8403326; as a result of this the shock resistance of the injector is improved.

The solvent by-pass may be provided in the barrel wall or in the passable stopper. In the latter case the passable stopper may comprise a non-return valve, permitting passage of liquid under the influence of a certain pressure exerted in one direction, but sealed when the direction of the pressure is reversed. Such a non-return valve is disclosed, for instance, in the German utility model (Gebrauchsmuster) No. G 8603917.2. When using a solvent by-pass in the barrel wall this solvent by-pass may be constructed in various manners. The barrel may be made of glass or a suitable synthetic material; in the latter case the barrel may be manufactured, for example, by injection moulding. When the barrel is of synthetic material, the by-pass in the barrel wall preferably comprises at least one slot recessed in the inner wall of the barrel and extending in the longitudinal direction of the barrel over a length slightly exceeding the length of the passable stopper. In another preferred embodiment the inner wall of the barrel comprises, at the area of the by-pass, at least one ridge which extends in the longitudinal direction of the barrel over a length which slightly exceeds the length of the passable stopper so that, when the injector is made ready for use, said stopper is deformed by contact with the ridge or ridges, a passage for the solvent behind said passable stopper being formed allowing said liquid to pass the stopper. Similar by-passes can also be provided in a glass barrel wall, but synthetic materials are better suitable for this purpose. A glass barrel is by far to be preferred to a barrel of a synthetic material because synthetic materials generally are less suitable than glass to store therein for a long period of time liquids intended to be injected; synthetic materials may contaminate the liquids or may adversely influence the stability of the said liquids. However, glass has for its disadvantage that it is fragile. The use of a sleeve of a shrinkable plastic sheet which is shrunk around the glass barrel, as disclosed in European Patent Application No. 107874, in particular as shown in FIG. 4 thereof, considerably improves the breaking strength of barrels of unhardened glass. The wall of a glass barrel can most simply be provided with a by-pass by deforming the wall of the barrel at the area of the by-pass over a length slightly exceeding the length of the passable stopper, so that, when the injector is made ready for use, the solvent behind this stopper can pass the stopper at the area of the deformation. The local deformation of the barrel wall preferably comprises at least on outwardly projecting longitudinal bulge of the barrel wall through which, when the injector is made ready for use, the solvent behind the passable stopper can reach the solid in front of this stopper, or comprises at least one inwardly projecting longitudinal ridge of the barrel wall as a result of which, when the injector is made ready for use, the passable stopper is deformed by contact with the ridge or ridges, a passage for the solvent behind the passable stopper being formed through which said liquid can reach the solid in front of said stopper past the stopper. The barrel wall may alternatively be deformed locally in such a manner that the barrel wall at that area has an oval cross-section, so that, when the injector is made ready for use, the solvent behind the passable stopper can reach the solid in front of said stopper.

A local deformation of the wall of the barrel in the form of one or more outwardly projecting longitudinal bulges is generally considered to be the best suitable solution for a by-pass in the glass barrel wall, because this can be provided very simply in a barrel wall and during operation of the injector constitutes a reliable passage for the solvent. When a collared needle holder is used, this ensures, together with the preferably used clamping sleeve to be described hereinafter and connected in a clamping manner around the rear end of the barrel, that such a bulge or such bulges in the glass barrel wall is or are protected from damage or fracture upon assembling the injector. By using a collared needle holder and a clamping sleeve, it is moreover not necessary to adapt the shape of the cartridge holder to the shape of the outwardly bent by-pass in the barrel, and the assembling, in particular the automatic assembling, of the cartridge in the holder is not impeded by the asymmetric cross-section of the barrel at the area of the by-pass.

The invention will be described in greater detail with reference to a preferred embodiment which is shown in the drawings, in which.

Figures 1, 2:
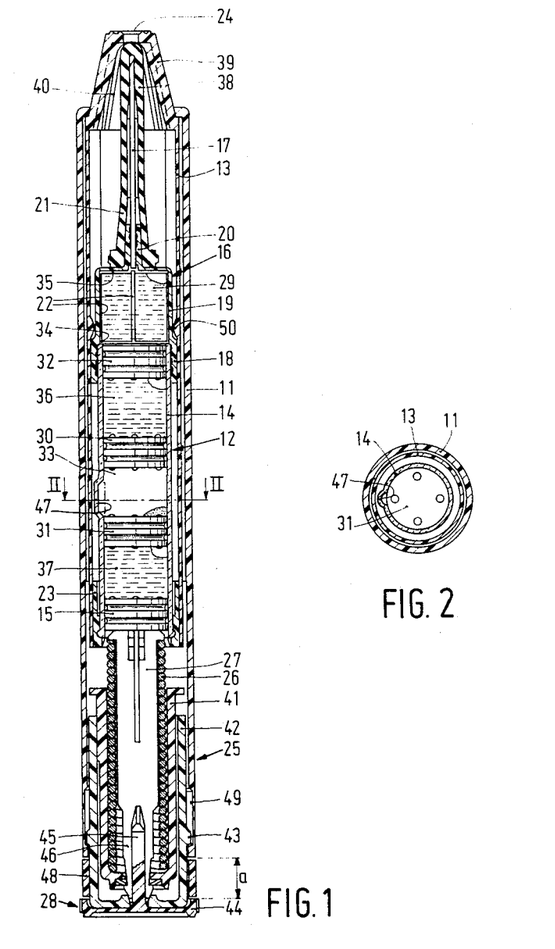
FIG. 1 is a longitudinal sectional view of an injector according to the invention in which, in addition to two injection liquids, a solid and a solvent therefor are accommodated separately, in the condition in which the injector can be transported and stored.
FIG. 2 is a cross-sectional view through the injector shown in FIG. 1 at the area of the by-pass in the barrel and that taken on the line II—II viewed in the direction of the passable stopper.

The injector shown in FIG. 1 is constructed for the greater part as described in U.S. Pat. No. 4,529,403 mentioned hereinbefore. In outline, the injector comprises a cylindrical outer sleeve 11 in which a cartridge holder 13 is rearwards movably provided, in which holder a cartridge 12 is accommodated, comprising a barrel 14, a piston 15 in one end of the barrel and a needle holder 16 at the other end. At the front end of the barrel the needle holder is connected by means of a collar 18. The needle holder further comprises a neck 20 in which an injection needle is connected, and a shaft 19 between collar and neck. The needle is covered in a sterile manner by a sleeve-like needle guard 21 of rubber. The closed end portion 38 of the rubber needle guard is narrowed internally and in this manner keeps the front end portion of the needle tightly enclosed. The front end portion of the needle guard may also be constructed so as to be solid, the tip of the needle being pierced into the solid rubber of the guard over such a distance that the needle aperture is fully sealed. Four longitudinal slots 22 are recessed in the side wall of the shaft 19 of the needle holder and adjoin slots 35 which are radially recessed in the rear face of the neck and which in their turn communicate with the open rear end of the injection needle. In the tapering nose portion 39 of the cartridge holder 13 a central aperture 24 is recessed. A clamping sleeve 23 which, like the collar 18 of the needle holder, is movable in the cartridge holder 13, is connected in clamping manner around the rear end of the barrel 14 by means of snap joint. The cartridge 12 is accommodated in the cartridge holder 13 in such a manner that the closed end of the sleeve-like needle guard 21 engages the end of the tapering nose portion 39 of the cartridge holder. A plurality of longitudinal ribs 40 in said nose portion ensure the rigidity and the centering of the needle with needle guard. In order to prevent any unintentional forward movement of the barrel with needle holder in the cartridge holder during making the injector ready for use, the inner wall of the cartridge holder 13 comprises a number of radially extending inward projections 50 which engage the outwardly projecting front end of the collar 18 of the needle holder. The outer sleeve 11 has such a length that the cartridge holder 13 with cartridge 12 is accommodated in the front part and the discharge mechanism 25 in the rear part. The discharge mechanism comprises an inner piston sleeve 41 having an outwardly bent flange at the front end which is spaced from the rear edge of the cartridge holder with clamping sleeve 23. The coiled spring 26 is locked within said inner pistol sleeve by means of a plunger 27 as described in British Patent Specification No. 1,449,986 mentioned hereinbefore. An outer pistol sleeve 42 is provided around the inner pistol sleeve so as to be slidable and is locked in the outer sleeve 11 against rearward movement by means of a radially outwards extending circumferential edge 43 engaging in a circumferential groove 49 in the inner wall of the outer sleeve. Said circumferential groove 49 extends forward in the wall of the outer sleeve over a distance which is considerably larger than the width of the circumferential edge 43 on the outer wall of the outer pistol sleeve. A safety device 28 the safety pin 45 of which extends between four resilient prongs 46 at the rear end of the plunger and in this manner protects the injector against unintentional actuation, comprises a cap 44 which engages the inwardly bent end of the outer pistol sleeve 42. The barrel 14 is divided into four separated compartments by two separating stoppers 32 and 30 and by a passable stopper 31, namely liquid compartments 29 and 36 which comprise injection liquids, a compartment 33 for the solid, and a compartment 37 for the solvent for said solid. The stoppers and the piston are provided in the barrel so as to be movable and sealing circumferentially on the inner wall and are manufactured from a slightly flexible material, preferably from a rubber of a pharmaceutical quality. The shaft 19 of the needle holder 16 is proportioned in such a way that the space 29 bounded by the rear face of the neck and the side wall of the shaft, apart from the slots in the shaft, has approximately the same or a slightly larger diameter than the inner wall of the barrel 14 and is slightly longer than the collective separating stoppers 30 and 32, so that said space 29 can be filled substantially entirely by the collective separating stoppers in their ultimate forward position; however, the ends 34 of the slots 22 adjoining the barrel remain uncovered. As stated, the solid is accommodated in compartment 33 between the rear separating stopper 30 and the passable stopper 31, and the solvent for the solid is accommodated in compartment 37 between the piston 15 and the passable stopper. The barrel 14 comprises a by-pass for solvent 47 in the form of a longitudinal bulge, more clearly visible in the cross-sectional view of FIG. 2. A locking clip 48 keeps the distance a between the front edge of the cap 44 of the safety device and the rear edge of the outer sleeve 11 fixed before the injector is made ready for use.

Figure 3:
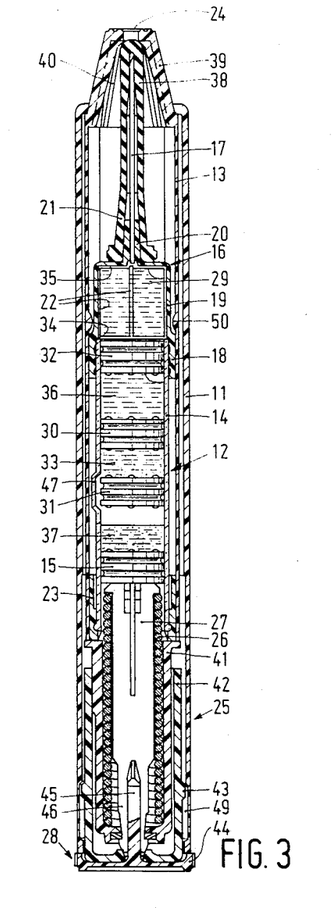
FIG. 3 illustrates the situation wherein the injector shown in FIG. 1 is being made ready for use, again the injector being shown in a longitudinal sectional view.
Figure 4:
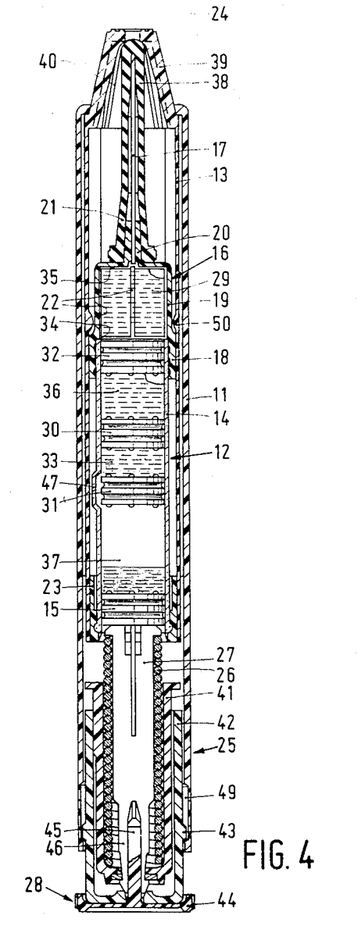
FIG. 4 illustrates the situation after the FIG. 3 injector has been made ready for use.

The injector shown in FIG. 1 is made ready for use by moving the discharge mechanism, after having removed the locking clip 48, forward over a distance a by means of the cap of the safety device; when the pressure on the cap is removed, the discharge mechanism is returned to its original position by the pressure built up in the injector. When the cap has been moved forward over the distance a, the pumping stroke, until the front edge of cap 44 engages the rear edge of the outer sleeve 11, the piston 15 and the passable stopper 31 have moved forward in the barrel. The rear end of the by-pass for solvent 47 has become accessible for the solvent in compartment 37, so that a quantity of solvent can flow to the solid in compartment 33. This situation is shown in FIG. 3. When the pressure on the cap 44 is removed, the piston 15 moves back again, approximately to its original position, under the influence of the compressed air in compartment 37. After "pumping" has been repeated approximately four times, in which the injector is held with its nose directed downwards, sufficient solvent has been added to the solid in compartment 33 to enable the solid to be dissolved sufficiently. A solution of the solid is now present in compartments 33 and 37 and may be used as an injection liquid. This situation is shown in FIG. 4, the injector being now ready for use.

Figure 5:
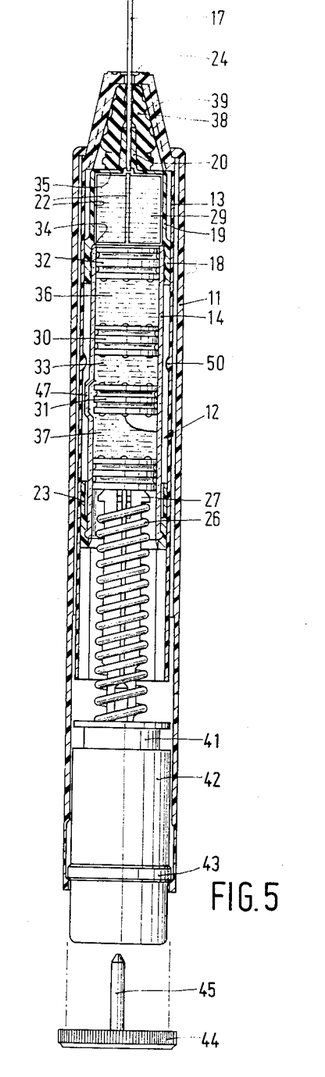
FIGS. 5 and 6 illustrate the operation of the same injector, ready for use as shown in FIG. 4, the injector being shown partly in a longitudinally sectional view and partly in a side elevation.
Figure 6:
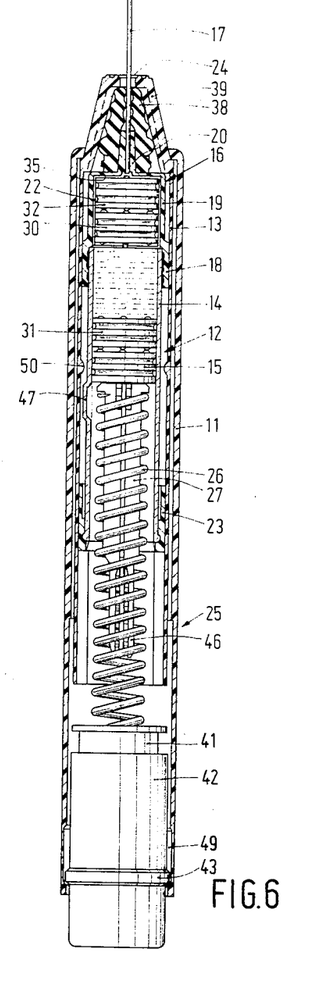

The injector which has been made ready for use may then be carried by the potential user and be used at any desired instant to administer an injection into his own body. For that purpose the safety member 28 is first removed by exerting a rearward directed force on the cap 44, as a result of which the safety pin 45 is pulled away from between the resilient prongs 46. By pressing the nose portion 39 of the cartridge holder against the body at the area where the injection is to be administered, the locking mechanism of the injector is unlocked. The rearward movement of the cartridge holder 13 in the outer sleeve 11 causes a rearward movement of the inner pistol sleeve in the outer pistol sleeve, as a result of which the discharge mechanism is unlocked, exactly as described in the British Patent Specification No. 1,449,986 mentioned hereinbefore. When the injector has been actuated, the barrel with contents and the needle holder with needle move forward, needle holder collar 18 and clamping sleeve 23 slidably moving forward in the cartridge holder. Upon passing the needle holder shaft, the cartridge holder wall is bent slightly outward at the area of the projections 50 so as to allow passage of the needle holder shaft ("overridden"). The needle guard is compressed between the front face of the needle holder neck and the rear face of the front end of the nose portion 39 of the cartridge holder 13, the needle 17 piercing the closed end of the needle guard, emanating through the aperture 24 in the nose of the cartridge holder, and penetrating into the user's body. When the needle is in its foremost position, as illustrated in FIG. 5, in which the needle holder is retained by a narrowing in the cartridge holder 13 at the area where the nose portion 39 begins, or by the force stored in the compressed needle guard, the forward movement of the piston begins under the influence of the same spring. First, injection liquid from compartment 29 is injected. At the instant at which the separating stopper 32 has moved forward over such a distance in the shaft of the needle holder that the entrance 34 to the slots 22 in the shaft of the needle holder is uncovered for the injection liquid in compartment 36, said liquid can reach the injection needle via the slots 22 and can be injected. During the same time the injection liquid in compartment 37 flows through solvent by-pass 47 into compartments 33, the passable stopper 31 remaining in its place, until the front face of the piston engages the rear face of the passable stopper. When all the injection liquid from compartment 36 has been injected, the front face of the separating stopper 30 engages the rear face of the separating stopper 32. Under the influence of the spring 26, said stoppers are collectively moved forward in the shaft of the needle holder. When the stopper 30 has moved forward over such a distance that the entrance 34 to the slots in the shaft of the needle holder is uncovered for the injection liquid in compartment 33, which situation is shown in FIG. 6, said liquid can finally also reach the injection needle via the slots 22 and 35 and can ultimately be injected. In the final situation, not shown in the Figures, the stoppers and the piston engage each other. The stoppers then are in their ultimate forward position, in which the front face of separating stopper 32 engages the front end wall of the needle holder shaft.

It will be apparent to those skilled in the art that various modifications and variations could be made in the automatic injector of the invention without departing from the scope or spirit of the invention.

What is claimed:

1. An automatic injector for injecting one or more injection liquids, in which, prior to use, different substances which are not allowed to be in contact with each other for a long period of time can be stored separately comprising an assembly of a discharge mechanism, a cartridge in a cartridge holder, and an outer sleeve which is telescopically slidable around the cartridge holder, the cartridge comprising:

a hollow, substantially cylindrical barrel which is open at its rear end, a piston which is movable in the barrel and seals same, a number of separating stoppers equal to one less than the number of injection liquids, said separating stoppers being movable in the barrel and having circumferences that adjoin the inner wall of the barrel in a sealing manner, thereby keeping the injection liquids in the barrel separated from each other prior to use of the injector, a needle holder connected to the front end of the barrel in a sealing manner and comprising a neck for sealingly gripping a needle, which injector is characterized in that one of the substances in the injector is solid and can be injected as an injection liquid after dissolving in a solvent, the discharge mechanism is in operative relationship with the piston via a plunger and its capable of telescoping movement relative to the cartridge holder, permitting the injector to be made ready for use by a single or repeated forward movement of the piston in the barrel, prior to using the injector, the cartridge at its front end is provided with a sealing means to prevent injection liquid from leaving the injector via the needle during making the injector ready for use, a passable stopper, movably provided in the barrel in front of the piston and which, prior to making the injector ready for use, adjoins the inner wall of the barrel in a circumferentially sealing manner and keeps the solid separated from the solvent, and a solvent by-pass for liquid is situated in the barrel wall over a length slightly exceeding the length of the passable stopper, said solvent by-pass permitting the solvent to pass the passable stopper and reach the solid in front of said stopper and dissolve same upon making the injector ready for use.

2. An injector as claimed in claim 1, characterized in that the injection needle is connected to the barrel by means of a needle holder which comprises a collar sealingly connecting the needle holder to the front end of the barrel and keeping the barrel in radially spaced relationship from the cartridge holder.

3. An injector as claimed in claim 2, characterized in that the injection needle is connected to the barrel by means of a needle holder, comprising a collar with which the needle holder is sealingly connected to the front end of the barrel, a neck in which the injection needle is connected, a hollow, substantially cylindrical shaft between collar and neck, and a by-pass for injection liquid in the wall of the shaft allowing the injection liquid or liquids behind the separating stopper or stoppers to reach the injection needle when during use of the injector the stopper or stoppers is or are moved forward into the shaft of the needle holder.

4. An injector as claimed in claim 3, characterized in that the by-pass for injection liquid in the wall of the shaft of the needle holder comprises at least one slot recessed in the inner wall of the shaft and extending from the rear end of the shaft in the longitudinal direction of the shaft, and communicating with the open rear end of the injection needle via at least one slot radially recessed in the rear face of the neck of the needle holder.

5. An injector as claimed in claim 3, characterized in that the inner wall of the shaft of the needle holder comprises at least one ridge extending from the rear end of the shaft in the longitudinal direction of the shaft, so that when using the injector the separating stopper or stoppers is or are deformed by contact with the said ridge, a passage for injection liquid behind the said stopper or stoppers being formed permitting said liquid to pass the stopper or stoppers, and that the rear face of the neck of the needle holder or the front face of the separating stopper or front separating stopper comprises a plurality of spacing supports allowing said liquid, after passing the stopper or stoppers, to reach the open rear end of the injection needle.

6. An injector as claimed in claim 1, characterized in that the by-pass for solvent in the barrel wall comprises at least one slot recessed in the inner wall of the barrel and extending in the longitudinal direction of the barrel over a length slightly exceeding the length of the passable stopper; or in that the inner wall of the barrel at the area of the solvent by-pass comprises at least one ridge which extends in the longitudinal direction of the barrel over a length slightly exceeding the length of the passable stopper, so that, when the injector is made ready for use, said stopper is deformed by contact with said ridge, a passage for the solvent behind said passable stopper being formed allowing said liquid to pass the stopper.

7. An injector as claimed in claim 1, characterized in that the wall of the barrel at the area of the solvent by-pass is deformed over a length slightly exceeding the length of the passable stopper, so that, when the injector is made ready for use, the solvent behind said stopper can pass the stopper at the area of the deformation; wherein said local deformation of the barrel wall comprises at least one outwardly projecting longitudinal bulge of the barrel wall through which, when the injector is made ready for use, the solvent behind the passable stopper can reach the solid in front of said stopper; wherein said local deformation of the barrel wall comprises at least one inwardly projecting longitudinal ridge of the barrel wall as a result of which, when the injector is made ready for use, the passable stopper is deformed by contact with said ridge, a passage for the solvent behind the passable stopper being formed through which said liquid can reach the solid in front of said stopper past the stopper; or wherein at the area of the deformation the wall of the barrel has an oval cross-section as a result of which, when the injector is made ready for use, the solvent behind the passable stopper can reach the solid in front of said stopper.

8. An automatic injector for injecting one or more injection liquids, in which prior to use, different substances which are not allowed to be in contact with each other for a long period of time can be stored separately, comprising an assembly of a discharge mechanism, a cartridge in a cartridge holder, and an outer sleeve which is telescopically slidable around the cartridge holder, the cartridge comprising:
- a hollow, substantially cylindrical barrel which is open at its rear end,
- a piston which is movable in the barrel and seals same,
- a number of separating stoppers equal to one less than the number of injection liquids, said separating stoppers being movable in the barrel and having circumferences that adjoin the inner wall of the barrel in a sealing manner, thereby keeping the injection liquids in the barrel separated from each other prior to use of the injector,
- a needle holder connected to the front end of the barrel in a sealing manner and comprising a neck for sealingly gripping a needle, which injector is characterized in that
- one of the substances in the injector is solid and can be injected as an injection liquid after dissolving in a solvent,
- the discharge mechanism is in operative relationship with the piston via a plunger and is capable of telescoping movement relative to the cartridge holder, permitting the injector to be made ready for use by a single or repeated forward movement of the piston in the barrel,
- prior to using the injector, the cartridge at its front end is provided with a sealing means to prevent injection liquid from leaving the injector via the needle during making the injector ready for use,
- a passable stopper, movably provided in the barrel in front of the piston and which, prior to making the injector ready for use, adjoins the inner wall of the barrel in a circumferentially sealing manner and keeps the solid separated from the solvent, and
- a solvent by-pass for liquid is situated in the passable stopper, said solvent by-pass permitting the solvent to pass the passable stopper and reach the solid in front of said stopper and dissolve same upon making the injector ready for use.

9. An injector as claimed in claim 1, or 8 characterized in that prior to using the injector the injection needle is covered by a sleeve-like needle guard of a resilient material which is connected with its open end around the neck of the neelde holder and which in the proximity of its closed end keeps the front end portion of the needle tightly enclosed.

10. An injector as claimed in claim 1 or 8, characterized in that the injector comprises means to prevent a forward movement of the cartridge in the cartridge holder during making the injector ready for use.

11. An injector as claimed in claim 1 or 8, which injector is destined for at least two injection liquids and comprises further a by-pass for injection liquid in front of said separating stoppers, for permitting injection liquid behind said stoppers to reach the injection needle when during use of the injector said stoppers are moved forward, said by-pass extending in the longitudinal direction over a distance slightly larger than that of the collection of said separating stoppers, so that said collection of stoppers in their ultimate forward position does not cover the rear end of said by-pass.

12. An injector as claimed in claim 11, characterized in that the by-pass for injection liquid comprises at least one radially outwardly projecting bulge of the barrel wall which extends in the longitudinal direction of the barrel; or in that the by-pass for injection liquid comprises at least one radially inwardly directed ridge on the inner wall of the barrel or a separate plastics fitting mounted within the wall of the barrel, said ridge or fitting extending in the longitudinal direction of the barrel and having a length slightly exceeding the length of the separating stopper or collection of separating stoppers, so that upon use of the injector said stopper or stoppers is or are deformed by contact with said ridge or fitting, a passage for the injection liquid or liquids behind said stopper or stoppers being formed, allowing said liquid or liquids to pass said stopper or stoppers.

13. An injector as claimed in claim 11, characterized in that prior to using the injector the injection needle is covered by a sleeve-like needle guard of a resilient material which is connected with its open end around the neck of the needle holder and which in the proximity of its closed end keeps the front end portion of the needle tightly enclosed.

14. An injector as claimed in claim 1 or 8, characterized in that the discharge mechanism can be moved telescopically relative to the outer sleeve comprising the cartridge holder locked therein against forward movement, so that by a single or repeated operation of inwardly telescoping the discharge mechanism relative to the outer sleeve, as a result of which the piston is moved forward in the barrel, the injector is made ready for use.

15. An injector as claimed in claim 14, characterized in that, prior to making the injector ready for use, one of the discharge mechanism and the cartridge holder is fixed relative to the outer sleeve by means of a detachable locking member for preventing unintentional movement of the discharge mechanism or the cartridge holder relative to said outer sleeve.

16. An injector as claimed in claim 1 or 8, characterized in that the cartridge holder is telescopically movable relative to the outer sleeve comprising the discharge mechanism locked therein against rearward movement, so that by a single or repeated operation of inwardly telescoping the cartridge holder relative to the outer sleeve, as a result of which the piston is moved forward in the barrel, the injector is made ready for use.

17. An injector as claimed in claim 16, characterized in that, prior to making the injector ready for use, one of the discharge mechanism and the cartridge holder is fixed relative to the outer sleeve by means of a detachable locking member fore preventing unintentional movement of the discharge mechanism or the cartridge holder relative to said outer sleeve.

* * * * *